(12) United States Patent
Hoshino et al.

(10) Patent No.: US 11,382,634 B2
(45) Date of Patent: Jul. 12, 2022

(54) EMBOLIC DEVICE SUITED FOR EASE OF DELIVERY AND PLACEMENT

(71) Applicant: AVANTEC VASCULAR CORPORATION, Sunnyvale, CA (US)

(72) Inventors: Ryan Hoshino, Sunnyvale, CA (US); Sith Khoune, Sunnyvale, CA (US); John To, Sunnyvale, CA (US); Jennifer Huynh, Sunnyvale, CA (US); Maria Cruz, Sunnyvale, CA (US)

(73) Assignee: Avantec Vascular Corporation, Sunnyvale, CA (US)

( * ) Notice: Subject to any disclaimer, the term of this patent is extended or adjusted under 35 U.S.C. 154(b) by 296 days.

(21) Appl. No.: 16/719,674

(22) Filed: Dec. 18, 2019

(65) Prior Publication Data

US 2021/0186513 A1    Jun. 24, 2021

(51) Int. Cl.
*A61B 17/12* (2006.01)

(52) U.S. Cl.
CPC .. *A61B 17/12113* (2013.01); *A61B 17/12145* (2013.01); *A61B 2017/12095* (2013.01)

(58) Field of Classification Search
CPC ........ A61B 17/12113; A61B 17/12145; A61B 2017/12095
See application file for complete search history.

(56) References Cited

U.S. PATENT DOCUMENTS

| | | |
|---|---|---|
| 5,137,288 A | 8/1992 | Starkey et al. |
| 5,396,902 A | 3/1995 | Brennen et al. |
| 5,464,300 A | 3/1995 | Crainich |
| 5,484,443 A | 1/1996 | Pascarella et al. |

(Continued)

FOREIGN PATENT DOCUMENTS

| | | |
|---|---|---|
| CN | 106943218 A | 7/2017 |
| EP | 2982317 A1 | 2/2016 |

(Continued)

OTHER PUBLICATIONS

Notification of International Search Report & the Written Opinion dated Jan. 11, 2019; Application No. PCT/US18/57369 filed Oct. 24, 2018; pp. 1-9.

(Continued)

*Primary Examiner* — Ryan J. Severson
*Assistant Examiner* — Mikail A Mannan
(74) *Attorney, Agent, or Firm* — FisherBroyles LLP; Kevin D. Jablonski

(57) ABSTRACT

An embolic device and a corresponding embolic device delivery system and method. In one example, an embolic device delivery system comprises a delivery catheter, a coupler disposed inside the delivery catheter, and an embolic device that may be carried and placed by the coupler. The embolic device includes a primary winding that forms a hollow tube such that a coupler may be threaded therethrough. Further, the embolic device may include a slotted metal tube suited to be affixed to one end of the hollow tube formed by the primary winding. Additionally, the embolic device may include a retaining mechanism that includes one or more protrusions suited to engage with one or more slots of the slotted metal tube. In this manner, the retaining mechanism is affixed to the slotted metal tube and the hollow tube formed by the primary winding.

17 Claims, 11 Drawing Sheets

(56) References Cited

U.S. PATENT DOCUMENTS

| | | |
|---|---|---|
| 5,562,629 A | 10/1996 | Haughton et al. |
| 5,601,568 A | 2/1997 | Chevillon et al. |
| 5,725,506 A | 3/1998 | Freeman et al. |
| 5,782,748 A | 7/1998 | Palmer et al. |
| 5,814,062 A | 9/1998 | Sepetka et al. |
| 5,993,470 A | 11/1999 | Yoon |
| 6,017,322 A | 1/2000 | Snoke et al. |
| 6,021,343 A | 2/2000 | Foley et al. |
| 6,053,934 A | 4/2000 | Andrews et al. |
| 6,165,180 A | 12/2000 | Cigaina et al. |
| 6,524,318 B1 | 2/2003 | Longhini et al. |
| 6,527,780 B1 | 3/2003 | Wallace et al. |
| 6,554,778 B1 | 4/2003 | Fleming, III |
| 6,575,919 B1 | 6/2003 | Reiley et al. |
| 6,613,014 B1 | 9/2003 | Chi |
| 6,632,091 B1 | 10/2003 | Cise et al. |
| 6,673,092 B1 | 1/2004 | Bacher |
| 6,716,223 B2 | 4/2004 | Leopold et al. |
| 6,764,499 B2 | 7/2004 | Honey et al. |
| 6,802,860 B2 | 10/2004 | Cosgrove et al. |
| 6,814,738 B2 | 11/2004 | Naughton et al. |
| 6,818,005 B2 | 11/2004 | Kupferschmid et al. |
| 6,887,246 B2 | 5/2005 | Bhatnagar et al. |
| 7,001,342 B2 | 2/2006 | Faciszewski |
| 7,018,394 B2 | 3/2006 | Diaz et al. |
| 7,306,574 B2 | 12/2007 | Massey et al. |
| 7,422,595 B2 | 9/2008 | Morris et al. |
| 7,645,272 B2 | 1/2010 | Chang et al. |
| 7,875,027 B2 | 1/2011 | Prevost et al. |
| 7,976,553 B2 | 7/2011 | Shelton, IV et al. |
| 7,988,615 B2 | 8/2011 | Anderson et al. |
| 7,993,329 B2 | 8/2011 | Howell et al. |
| 8,114,118 B2 | 2/2012 | Knodel et al. |
| 8,204,604 B2 | 6/2012 | Kuzma et al. |
| 8,337,502 B2 | 12/2012 | Bastian et al. |
| 8,702,625 B2 | 4/2014 | Ayala et al. |
| 8,764,762 B2 | 7/2014 | Blain et al. |
| 8,852,178 B2 | 10/2014 | Thompson et al. |
| 8,998,887 B2 | 4/2015 | Simmen et al. |
| 9,011,412 B2 | 4/2015 | Albritton, IV et al. |
| 9,017,369 B2 | 4/2015 | Renger et al. |
| 9,095,365 B2 | 8/2015 | Kaercher et al. |
| 9,108,022 B2 | 8/2015 | Ogle |
| 9,119,645 B2 | 9/2015 | McBride |
| 9,168,058 B2 | 10/2015 | Duperier et al. |
| 9,192,398 B2 | 11/2015 | Siravo et al. |
| 9,247,948 B2 | 2/2016 | Pinkowski et al. |
| 9,308,349 B2 | 4/2016 | Rezac et al. |
| 9,463,036 B2 | 10/2016 | Brady et al. |
| 9,498,603 B2 | 11/2016 | Parodi et al. |
| 9,539,413 B2 | 1/2017 | Ogle |
| 9,549,718 B2 | 1/2017 | Schneider et al. |
| 9,615,951 B2 | 1/2017 | Bennett et al. |
| 9,636,138 B2 | 5/2017 | Schneider |
| 9,642,982 B2 | 5/2017 | Milijasevic et al. |
| 9,700,322 B2 | 6/2017 | Dias et al. |
| 9,700,318 B2 | 7/2017 | Scirica et al. |
| 9,775,621 B2 | 10/2017 | Tompkins et al. |
| 9,919,412 B2 | 3/2018 | Petit |
| 9,943,313 B2 | 4/2018 | Jones et al. |
| 9,955,991 B2 | 5/2018 | Riva |
| 10,052,108 B2 | 8/2018 | Aguilar et al. |
| 10,058,350 B2 | 8/2018 | Geist |
| 10,112,031 B2 | 10/2018 | Matthiassen |
| 10,118,027 B2 | 11/2018 | Seifert et al. |
| 10,149,676 B2 | 12/2018 | Mirigian et al. |
| 10,335,156 B2 | 7/2019 | Islak et al. |
| 2003/0032941 A1 | 2/2003 | Boyle et al. |
| 2003/0093085 A1 | 5/2003 | Leopold et al. |
| 2005/0137585 A1 | 6/2005 | Landman et al. |
| 2005/0177182 A1 | 8/2005 | Burg et al. |
| 2006/0004398 A1 | 1/2006 | Binder, Jr. et al. |
| 2006/0149127 A1 | 7/2006 | Seddiqui et al. |
| 2006/0276829 A1 | 12/2006 | Balgobin et al. |
| 2007/0010843 A1 | 1/2007 | Green |
| 2007/0239196 A1 | 10/2007 | Pomeranz |
| 2008/0045997 A1 | 2/2008 | Balgobin et al. |
| 2008/0119887 A1 | 5/2008 | Que et al. |
| 2008/0287971 A1 | 11/2008 | Kuntz |
| 2009/0099566 A1 | 4/2009 | Maness et al. |
| 2009/0118737 A1 | 5/2009 | Pernot et al. |
| 2009/0138023 A1 | 5/2009 | Johnson et al. |
| 2009/0240258 A1 | 9/2009 | Kuzma et al. |
| 2009/0306544 A1 | 12/2009 | Ng et al. |
| 2010/0094395 A1* | 4/2010 | Kellett ............ A61B 17/12145 623/1.11 |
| 2010/0191225 A1 | 7/2010 | Leonard |
| 2011/0046660 A1 | 2/2011 | Syed et al. |
| 2011/0295303 A1 | 12/2011 | Freudenthal |
| 2013/0211201 A1 | 8/2013 | Wongsiri |
| 2013/0282007 A1 | 10/2013 | Chong et al. |
| 2014/0094894 A1 | 4/2014 | Forde et al. |
| 2015/0025566 A1 | 1/2015 | Win et al. |
| 2015/0099997 A1 | 4/2015 | Cabiri |
| 2015/0119924 A1* | 4/2015 | Que ................. A61B 17/12022 606/200 |
| 2015/0202410 A1 | 7/2015 | Odeh |
| 2015/0230785 A1 | 8/2015 | Devere, Jr. et al. |
| 2015/0327868 A1 | 11/2015 | Islak et al. |
| 2016/0038150 A1 | 2/2016 | Lorenzo |
| 2016/0143649 A1 | 5/2016 | Weekes |
| 2016/0175112 A1 | 6/2016 | Pruvost et al. |
| 2016/0256667 A1 | 9/2016 | Ribelin et al. |
| 2017/0027659 A1 | 2/2017 | Goddard et al. |
| 2017/0105739 A1* | 4/2017 | Dias ................. A61B 17/1214 |
| 2017/0252057 A1 | 9/2017 | Bonnette et al. |
| 2017/0367714 A1 | 12/2017 | Mcculloch et al. |
| 2018/0085174 A1 | 3/2018 | Radtke et al. |
| 2018/0200496 A1 | 7/2018 | Kratzberg et al. |
| 2018/0221011 A1 | 8/2018 | Malkowski |
| 2018/0228493 A1 | 8/2018 | Aguilar et al. |
| 2018/0296799 A1 | 10/2018 | Horst et al. |
| 2018/0317924 A1 | 11/2018 | Aguilar et al. |
| 2019/0015146 A1 | 1/2019 | Dubois |
| 2019/0083179 A1 | 3/2019 | Kheradpir et al. |
| 2020/0229957 A1 | 7/2020 | Bardsley et al. |

FOREIGN PATENT DOCUMENTS

| | | |
|---|---|---|
| JP | 3016559 B2 | 3/2000 |
| JP | 4220237 B2 | 2/2009 |
| JP | 4224124 B1 | 2/2009 |
| JP | 6205438 B2 | 9/2017 |
| JP | 6306706 B2 | 4/2018 |
| JP | 6370605 B2 | 8/2018 |
| JP | 6391710 B2 | 9/2018 |
| JP | 2018153460 A | 10/2018 |
| JP | 6419779 B2 | 11/2018 |
| WO | 2019094197 A1 | 5/2019 |

OTHER PUBLICATIONS

Penumbra; "Embolization System"; https://www.penumbrainc.com/wp-content/uploads/2018/09/11533C_PenumbraEmbolizationSystem_Trifold_USA_22Aug18_SinglePage_PREVIEW.pdf; (2018).

Binder et al.; American College of Cardiology Foundation; "Transcatheter Aortic Valve Replacement With a New Self-Expanding Transcatheter Heart Valve and Motorized Delivery System"; vol. 6, No. 3, (Mar. 2013).

Wiegerinch et al.; Taylor & Francis Group; "An up-to-date overview of the most recent transcatheter implantable aortic valve prostheses"; Expert Review of Medical Devices; Nov. 15, 2015.

Young et al.; "A Decade Later, Continued Transformation of Transcatheter Aortic Valve Replacement"; USC Cardiology Review; vol. 12, Issue 1 (2018).

European Patent Office; Extended European Search Report dated May 21, 2021; EPO Application No. 18876764.4; pp. 1-40 (2021).

(56) References Cited

OTHER PUBLICATIONS

Notification of International Search Report & the Written Opinion; dated Mar. 8, 2021; Application No. PCT/US20/61220 filed Nov. 19, 2020; pp. 1-11.

* cited by examiner

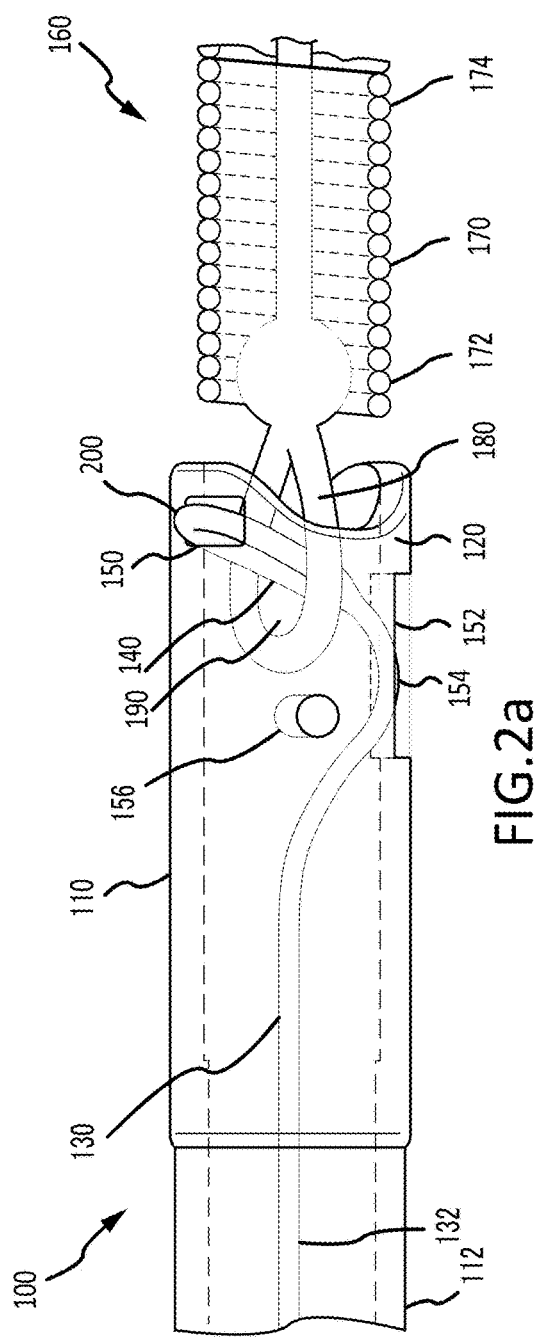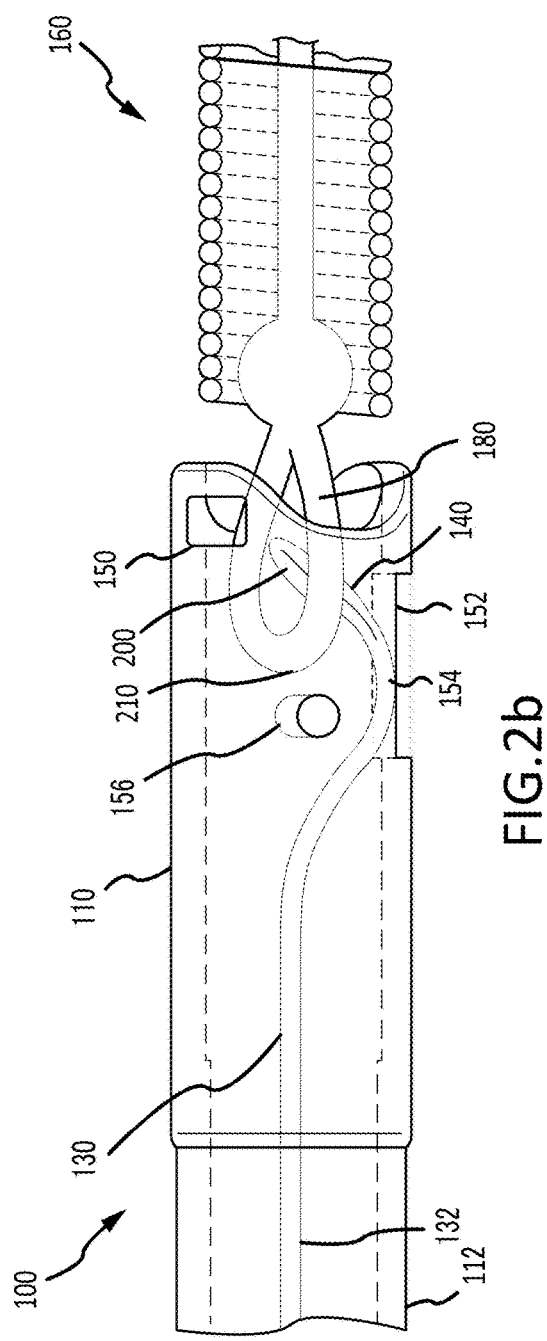

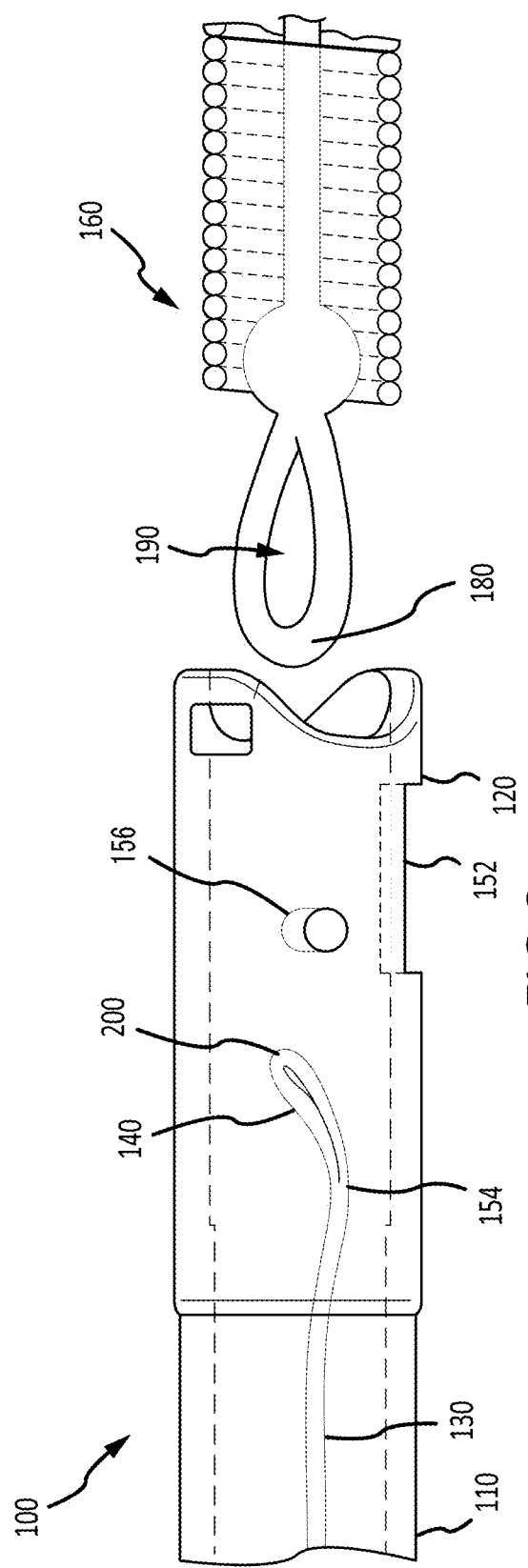
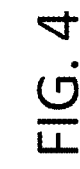
FIG. 2c
FIG. 4
FIG. 3

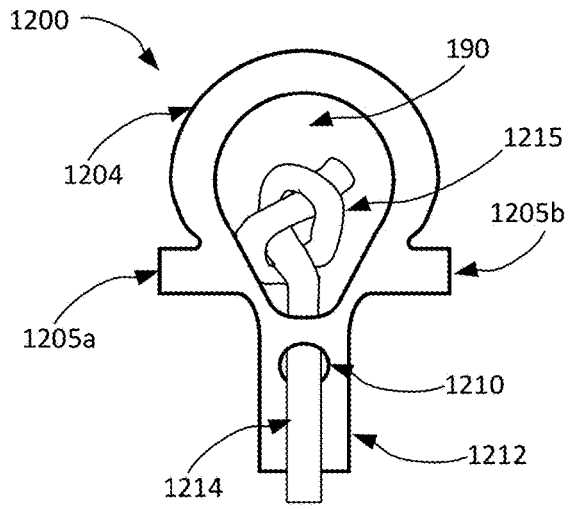
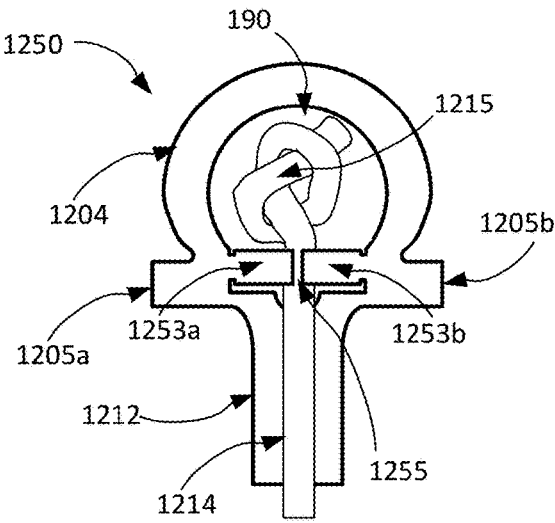
FIG. 12(a)          FIG. 12(b)
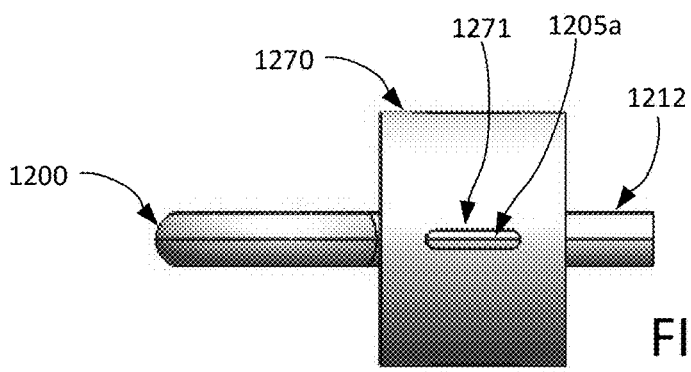
FIG. 12(c)
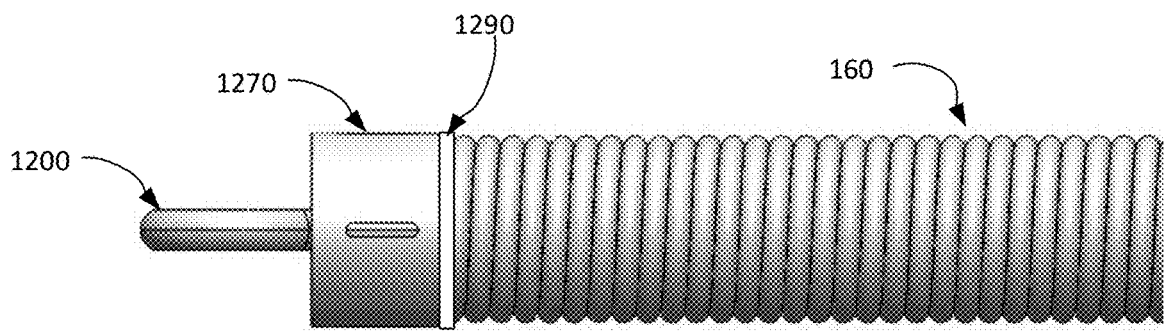
FIG. 12(d)

EMBOLIC DEVICE SUITED FOR EASE OF DELIVERY AND PLACEMENT

BACKGROUND

An aneurysm is a blood bulge formed in a wall of an artery and can develop in any artery, including brain, aorta, legs, and spleen. Various aneurysms are typically formed in a saccular form and if the saccular aneurysm ruptures, a stroke, also known as a subarachnoid hemorrhage, may occur. Open surgery to clip or seal the aneurysm is an option for treating and removing an aneurysm; however, the surgery often carries risks and may be inappropriate or dangerous for larger sizes of aneurysms and/or aneurysms in more sensitive locations. Therefore, treating, reducing, and/or removing aneurysms is important to the long-term health of patients.

As an alternative to open surgery, a surgeon may perform a minimally invasive procedure whereby an occlusion embolic device is placed within an artery in an effort to treat the developed aneurysm. In such a procedure, the occlusion embolic device (e.g., a blocking device) is placed into the saccular aneurysm at a position to isolate or block the saccular aneurysm from a blood vessel. The placement of the occlusion embolic device is typically accomplished using a catheter carrying the occlusion embolic device such that the device may be inserted into a blood vessel and steered through the blood vessel to treat the aneurysm.

Conventional embolic device deployment systems exhibit difficulties with respect to embolic device placement as maneuvering, placing and releasing the embolic device within an artery inside a patient's body and are proven to be cumbersome. Further, conventional embolic devices themselves may be difficult to engage, maneuver, and place using such conventional delivery systems. This is especially true for brain aneurysms as the deployment procedure requires accurate placement of the embolic device and any error during the procedure may result in significant damage to the brain.

BRIEF DESCRIPTION OF THE DRAWINGS

Aspects and many of the attendant advantages of the claims will become more readily appreciated as the same become better understood by reference to the following detailed description, when taken in conjunction with the accompanying drawings, wherein:

FIGS. 2(a)-(c) are diagrams of an embolic device delivery system according to an embodiment of the subject matter disclosed herein;

FIG. 3 is a diagram of a maneuverable tip of a coupler extending through an upper locking window of an embolic device delivery system shown in FIGS. 2(a)-(c) according to an embodiment of the subject matter disclosed herein;

FIG. 4 is a diagram of a maneuverable tip of a coupler protruding through a lower locking window of an embolic device delivery system shown in FIGS. 2(a)-(c) according to an embodiment of the subject matter disclosed herein;

FIGS. 12(a)-(d) are diagrams of additional embolic devices suited for ease of delivery and placement according to a still further embodiment of the subject matter disclosed herein.

Note that the same numbers are used throughout the disclosure and figures to reference like components and features.

DETAILED DESCRIPTION

Figure 1A:
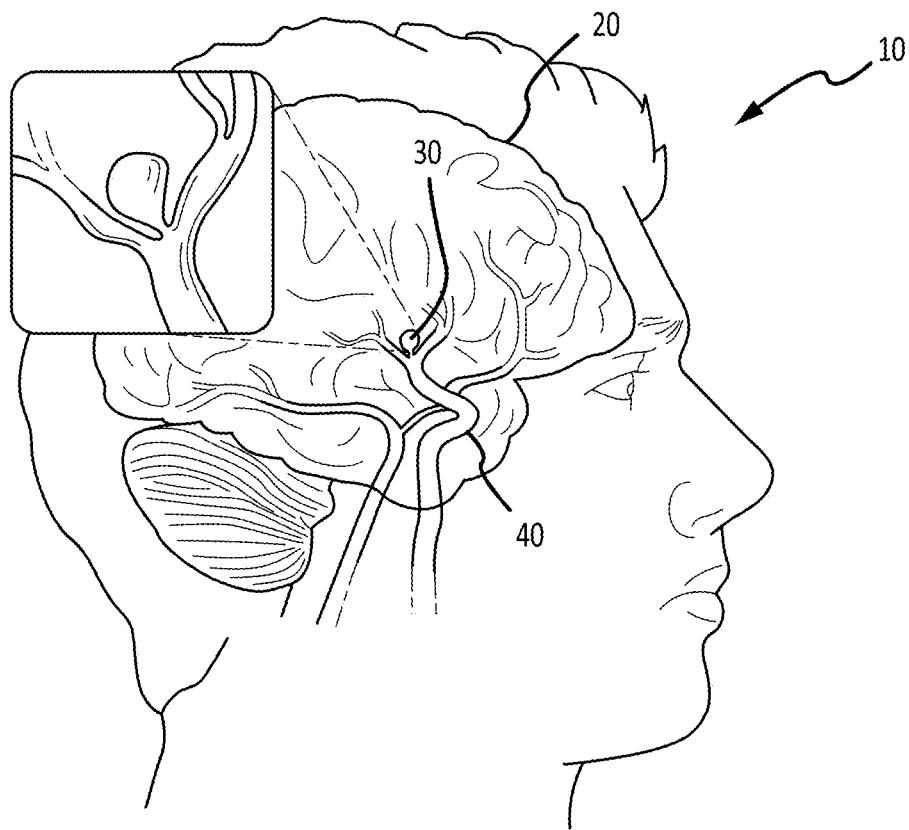
FIG. 1(a) is a perspective diagram of a patient with a brain aneurysm.

The subject matter of embodiments disclosed herein is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Embodiments will be described more fully hereinafter with reference to the accompanying drawings, which form a part hereof, and which show, by way of illustration, exemplary embodiments by which the systems and methods described herein may be practiced. The embolic device delivery system may, however, be embodied in many different forms and should not be construed as limited to the embodiments set forth herein; rather, these embodiments are provided such that this disclosure will satisfy the statutory requirements and convey the scope of the subject matter to those skilled in the art.

By way of an overview, the subject matter disclosed herein may be directed to an embolic device and a corresponding embolic device delivery system and method. In an embodiment, e.g., an embolic device delivery system comprises a delivery catheter, a coupler disposed inside the delivery catheter, and an embolic device that may be carried and placed by the coupler. In one embodiment, the embolic device includes a primary winding that forms a hollow tube such that a coupler may be threaded therethrough. Further, the embolic device may include a slotted metal tube suited to be affixed to one end of the hollow tube formed by the primary winding. Additionally, the embolic device may include a retaining mechanism that includes one or more protrusions suited to engage with one or more slots of the slotted metal tube. In this manner, the retaining mechanism is affixed to the slotted metal tube and the hollow tube formed by the primary winding in such a way as to allow ease of maneuverability when the retaining mechanism is engaged by a coupler of a delivery catheter that may be part of an embolic procedure system. Additional embodiments may include embolic devices having integral retaining mechanisms as well as retaining mechanisms secured to the primary winding without use of a slotted metal tube.

The delivery catheter may be a hollow tube such that the coupler can be slidably disposed inside of the tube with coil engagement mechanism disposed toward the distal end of the tube. In one embodiment, the coupler may be an elongated shape having a loop portion for engaging the coil toward the distal end of the delivery catheter. The loop portion of the coupler may be an elastic material or a shape-memory alloy, such as Nitinol or nickel titanium, such that the loop portion is bendable at various angles. Together, the delivery catheter and coupler may be inserted into an artery and carry an embolic device to an aneurysm for placement near and treatment of the aneurysm.

These and other advantages will become more apparent in the detailed descriptions below with respect to FIGS. 1-12.

Embolic Device Delivery System

Figure 1B:
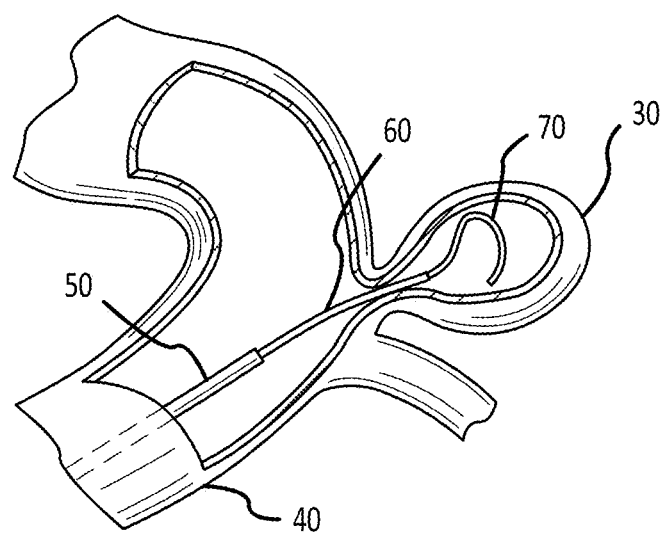
FIG. 1(b) shows the brain aneurysm of FIG. 1(a) in greater detail during treatment.

FIG. 1(a) is a perspective diagram of a patient 10 with a brain aneurysm 30. An aneurysm may be formed in any artery of a human body including the heart and the brain. An aneurysm that forms in blood vessels (e.g., arteries) 40 in the brain 20 is called a cerebral aneurysm or brain aneurysm 30. In this example, the brain aneurysm 30 resembles a balloon. Since the aneurysm 30 is caused due to the weakness of the artery, an aneurysm 30 with or near a thin artery wall 40 may rupture. A ruptured aneurysm (not shown) significantly contributes to the occurrence of a stroke and should be treated prior to rupture. FIG. 1(b) shows the brain aneurysm of FIG. 1(a) in greater detail and in the midst of a procedure using an embolic delivery device. The embolic device deployment system of FIG. 1(b) contains a deployment catheter 50 and, on occasion, a micro catheter 60 inside of the deployment catheter 50. The conventional embolic deployment system is inserted into the artery 40 and passed through the artery 40 to reach the desired location. At the desired location, the deployment catheter 50 and/or micro catheter 60 releases an embolic device 70 into the inside of the aneurysm 30 or near the aneurysm 30.

Depending on the location or nature of the aneurysm 30, the embolic device 70 is placed inside of the saccular aneurysm 30 as shown in FIG. 1(b) or the neck of the aneurysm to prevent further blood flow going into the aneurysm 30. The deployment mechanism of the embolic device 70 may include pushing off the embolic device 70 from the deployment catheter 50 as shown in FIG. 1(b); using a thread or fiber (not shown) for engaging the embolic device 70 and cutting off the thread or fiber when disengaging the embolic device 70; using a pressure (not shown), heat (not shown), or electricity (not shown) for releasing the embolic device 70; and unlocking an interlocking mechanism to release the embolic device 70 from the deployment catheter 50 (not shown). The interlocking mechanism of the embolic device delivery system typically interlocks an embolic device 70 with a portion of the deployment catheter 50 to carry the embolic device 70 through the inside of the artery 40 such that the deployment catheter 50 maneuvers the artery 40 with the embolic device 70 firmly coupled to the deployment catheter 50. However, the interlocking mechanisms in the conventional embolic device deployment systems require many components or features to achieve reliability, such as firmly holding the embolic device until the deployment catheter 70 reaches a desired location for effectively releasing the embolic device 70. Many conventional interlocking mechanisms require an additional locking component to interlock the deployment catheter 50 and embolic device 70 in a fixed manner. Nonetheless, having many components to achieve the reliability and smooth delivery counteract a goal of consistent and reliable delivery due to the highly likelihood of the irregularity or malfunction of the deployment system, which leads to a critical error in the procedure.

FIGS. 2(a)-(c) are diagrams of an embolic device delivery system 100 according to an embodiment of the subject matter disclosed herein. FIG. 2(a) shows an embolic device 160 coupled to a delivery catheter 110 in one embodiment. The delivery catheter 110 may include a proximal end 112 and distal end 120 along an axis (not shown) of the delivery catheter 110. When the distal end 120 of the delivery catheter 110 is inserted into an artery, the distal end 120 may be navigated through an artery to reach a desired location (e.g., a location of the aneurysm). Because the distal end 120 of the delivery catheter 110 is navigated through an artery, the embolic device 160 should be firmly coupled to the distal end 120 of the delivery catheter 110. The delivery catheter 110 may be designed as an elongated cylinder with a hollow interior tube extending from the proximal end 112 to the distal end 120. Since the delivery catheter 110 maneuvers through an artery, flexible materials may be used for the delivery catheter 110 as an elongated cylinder. In one embodiment, the flexible materials for the delivery catheter 110 may include a silicone, polyurethane (PU), polyethylene (PE), polyvinylchloride (PVC), polytetrafluoroethylene (PTFE), Polyetheretherketone (PEEK), nylon, as well as metallic catheter components, such as helical hollow stranded tubing, and laser cut flexible tubing. The flexible materials for the delivery catheter 110 may include a helical hollow Strand™ and can be obtained from Fort Wayne Metals, Fort Wayne, Iowa.

The elongated cylinder of the delivery catheter 110 further includes a coupler 130 disposed along a central axis of the delivery catheter 110. The coupler 130 may have a proximal end 132 and distal end 140. In one embodiment, the proximal end 132 of the coupler 130 may be a linear member that extends through the proximal end 112 of the delivery catheter 110. The proximal end 132 may further include a mechanism for a surgeon to actuate the coupler 130 by moving the coupler 130 backward inside the delivery catheter 110, further discussed below in FIG. 5. The linear member of the coupler 130 may also form an engagement member toward the distal end 140 of the coupler 130. In one embodiment, the engagement member 140 may be formed as a small diameter loop made of a shape-memory alloy, such as Nitinol, NiTi, or nickel titanium. The shape-memory alloy possesses super elasticity and unique memory characteristics of the original shape. Thus, the shape-memory alloy may be stretched and maintained in the stretched phase; however, once the alloy is released from the stretch, the alloy will return back to the original shape. The maneuverable engagement member 140 may be further configured to be become more/less rigid and/or more/less flaccid when exposed to heat, electricity, or physical force. As discussed with respect to FIGS. 2(b) and 2(c), this allows the coupler 130 to engage, maneuver and disengage an embolic device 160 during an embolic device delivery procedure.

The embolic device 160 coupled to the delivery catheter 110 may include an embolic device 160 configured to expand once placed at the appropriate location inside the artery or near the aneurysm. In some embodiments, the embolic device 160 may be a platinum coil. The embolic device 160 may also include a proximal end 172 and a distal end 174 and a retaining mechanism 180 may be formed at the proximal end 172 of the embolic device 170 to securely couple with the delivery catheter 110. In various embodiments, the retaining mechanism 180 may be formed as a closed ring, loop, hoop, or eyelet separately formed from the embolic device 160 and affixed at the proximal end 172 of the embolic device 160. (See below with respect to FIG. 10(a)-(c)), In a further embodiment, the retaining mechanism 180 may be formed integrally with the embolic device 160. (See below with respect to FIG. 11). With such a proximal end 172 suited to engage a coupler 130, the retaining mechanism 180 forms an aperture 190 by which the proximal end 172 of the coupler may engage and penetrate. The retaining mechanism 180 may be made of polypropylene or a platinum filament from the primary wind of the coil. During embolic device placement and delivery, the retaining mechanism 180 (and at times, the entire embolic device 160) may be disposed inside the delivery catheter 110 near the distal end 120. Thus, the diameter of the aperture 190 and the width of the embolic device 160 may be narrower than the inside diameter of the delivery catheter 110 such that the retaining mechanism 180 and embolic device 160 are held inside the distal end 120 of the delivery catheter 110 while being maneuvered through an artery.

When the delivery catheter 110 engages with the embolic device 160, the maneuverable engagement member 140 of the coupler 130 engages with the retaining mechanism 180 at the distal end 120 of the delivery catheter 110 by extending the maneuverable engagement member 140 into the aperture 190 of the retaining mechanism 180. For this configuration, the inside diameter of the aperture 190 may be slightly wider than the diameter of the maneuverable engagement member 140 such that the retaining mechanism 180 allows a small amount of movement for the maneuverable engagement member 140 to move around the inside of the aperture 190 of the retaining mechanism 180. In one embodiment, the maneuverable engagement member 140 may be extended upwardly through the aperture 190 by taking an upwardly curved shape. The maneuverable engagement member 140 may be extended downwardly or sideways instead of upwardly in response to rotation of the delivery catheter 110 due to manipulation of the delivery catheter by a surgeon such that a person having an ordinary skill in the art would change the direction of the curves accordingly. In a further embodiment, the maneuverable engagement member 140 maneuver away from the axis of the delivery catheter 110. Due to the super elasticity and shape memory characteristics of the maneuverable engagement member 140, the maneuverable engagement member 140 is capable of deforming its shape, such as from a straight configuration to an upwardly curved shape. In a further embodiment, the maneuverable engagement member 140 may be bent vertically at one portion to extend through the aperture 190 of the retaining mechanism 180.

As discussed briefly above, the delivery catheter 110 forms an upper locking window 150 on one side of the interior wall of the hollow tube near the distal end 120 of the delivery catheter 110 and a lower locking window 152 on the other side of the interior wall of the hollow tube near the distal end 120 of the delivery catheter 110. In one embodiment, the maneuverable engagement member 140 may form a U-shaped curve 154 and the downward curve 154 of the maneuverable engagement member 140 may be maintained with the locking features by the upper locking window 150 and the lower locking window 152. In this configuration, the bottom of the downward curve 154 of the maneuverable engagement member 140 may be maintained within the lower locking window 152 and the tip 200 of the maneuverable engagement member 140 may be maintained within the upper locking window 150 within the delivery catheter 110 while navigating the delivery catheter 110 into an artery. In another embodiment, the upper locking window 150 is located nearer to the distal end 120 of the delivery catheter 110 than the lower locking window 152 is to the distal end 120 of the delivery catheter 110 such that the maneuverable engagement member 140 is locked with the upper locking window 150 and the lower locking window 152 at the distal end 120 of the delivery catheter 110. FIGS. 3 and 4 show cutaway diagrams of the portions of the maneuverable engagement member 140 of the coupler 130 that extends through the upper locking window 150 and the lower locking window 152 of the delivery catheter 110 shown in FIGS. 2(a)-(c) according to an embodiment of the subject matter disclosed herein. Specifically, FIG. 3 describes a left elevational view of an upper locking window 150 of the delivery catheter 110 and FIG. 4 describes a front elevational view of the lower locking window 152 of the delivery catheter 110. When the embolic device 160 is in a position coupled to the delivery catheter 110 (see FIG. 2(a)), the maneuverable engagement member 140 engages with the aperture 190 of the retaining mechanism 180 and may be further extended through the upper locking window 150 located above the position of the aperture 190 of the retaining mechanism 180 and the lower locking window 152 to secure the maneuverable engagement member 140 in the position. When the tip 200 of the maneuverable engagement member 140 passes through the lower locking window 152 and reaches the upper locking window 150, the maneuverable engagement member 140 further curves up such that the tip 200 of the maneuverable engagement member 140 extends through the upper locking window 150. In a further embodiment, the maneuverable engagement member 140 may bend vertically to extend through the upper locking window 150 as well. Once the maneuverable engagement member 140 is shaped in the upwardly curved position, the maneuverable engagement member 140 maintains its shape until any physical force is applied to the maneuverable engagement member 140. The upwardly curved shape of the maneuverable engagement member 140 may be formed by physically bending the maneuverable engagement member 140, such as by hand, or by maneuvering the distal end 120 of the coupler 130 to extend the maneuverable engagement member 140 through the aperture 190 such that the straight original configuration is deformed into the curved shape. In various embodiments, the upper locking window 150 and lower locking window 152 may be formed as a rectangular shape, elliptical shape, oval shape, or round shape. In a still further embodiment, the width of the locking window 150 may be slightly wider than the width of the tip 200 of the maneuverable engagement member 140. As such, the inside of the locking window 150 allows limited movement of the tip 200 to move around such that the tip 200 is secured in the locking window 150.

In addition to the locking mechanisms by the upper and lower locking windows 150, 152, a cross bar 156 extending perpendicular to the axis of the hollow tube of the delivery catheter 110 may further limit the movements of the coupler 130 both in the distal direction 140 and proximal direction 132. When the embolic device 160 is in a position coupled to the delivery catheter 110 (see FIG. 2(*a*)), the coupler 130 may be slid toward the distal direction. However, during the sliding, the curve of the maneuverable engagement member 140 contacts with the cross bar 156 and prevents further movement in the distal direction. Further, when the coupler 130 moves proximally, the retaining mechanism 180 and maneuverable engagement member 140 may make contact with the cross bar 156 such that further movement in the proximal direction 132 may be prevented.

Figure 5:
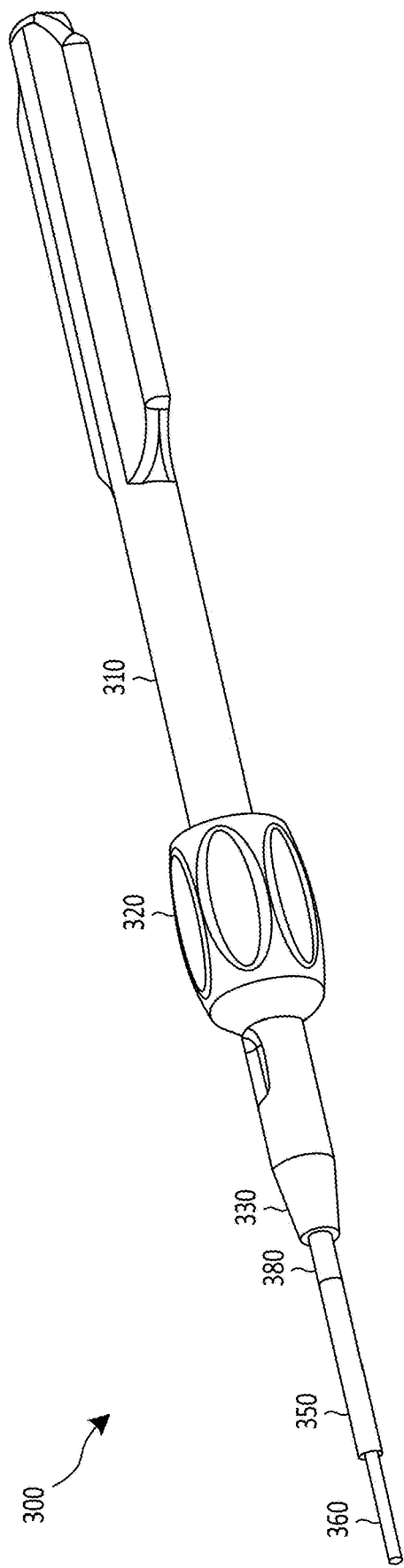
FIG. 5 is a diagram of an actuator handle connected to a proximal end of an embolic device delivery system shown in FIGS. 2(a)-(c) according to an embodiment of the subject matter disclosed herein.

FIG. 5 shows an actuation mechanism or handle 300 connected to a proximal end 112 of an embolic device delivery system 100 shown in FIGS. 2(*a*)-(*c*) according to an embodiment of the subject matter disclosed herein. The actuation handle 300 for maneuvering the coupler 130 of the delivery catheter 110 to release an embolic device 160 from the coupler 130 described in FIGS. 2(*a*)-2(*c*). The actuation handle 300 may be any suitable means by which a surgeon may easily maneuver the coupler 130 in the lineal direction within an artery of a patient. In one embodiment, the handle 300 is a simple mechanical handle 250 that can pull the coupler in the distal direction. In FIG. 5, the actuator handle 300 is shown including a distal member 310, proximal member 330, rotating barrel 320, outer shaft 350, and inner shaft 360. Those components 310, 320, 330, 350, and 360 are coupled each other. In another embodiment, an adhesive may be placed between outer shaft 350 and proximal member 330 such that the outer shaft 370 is stably fixed to the proximal member 330. The actuator handle 330 is designed for a surgeon to hold the distal member 310 in his/her hand such that the rotating barrel 320 can be held by a forefinger and thumb of the surgeon to rotate in right or left directions. In one embodiment, rotating the rotating barrel 320 in the left direction may extend the inner shaft 360 to the proximal direction and rotating the rotating barrel 320 in the right direction may shorten the inner shaft 360 in the distal direction.

Figure 6:
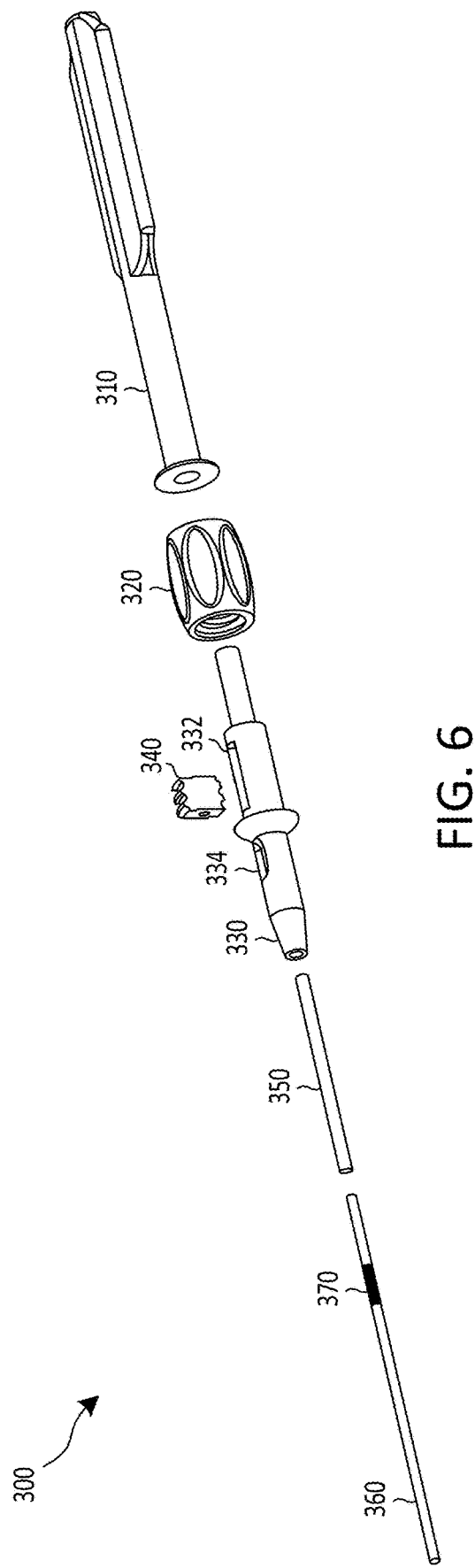
FIG. 6 is an exploded view of the actuator handle of FIG. 5 according to an embodiment of the subject matter disclosed herein.

FIG. 6 shows an exploded view of the actuation handle 300 of FIG. 5. The distal member 310 is directly coupled to the rotating barrel 320 and may be coupled by way of screw structure formed inside of the retaining barrel 320. The proximal member 330 has two windows, a view window 334 and shuttle window 332. A shuttle 340 is placed within the shuttle window 332 and moves from the distal direction to the proximal direction. In one embodiment, the shuttle 340 may move from the distal direction to the proximal direction when the rotating barrel 320 is rotated to the left direction. The shuttle 340 is connected to the inner shaft 360 such that the movement of the rotating barrel 320 to the left direction extends the inner shaft 360 to the proximal direction by way of moving the shuttle 340 into the proximal direction. The view window 334 may use a marker to slide within the view window 334 such that a surgeon can see how much the inner shaft 360 has moved to the proximal direction. On the other hand, the outer shaft is coupled to the proximal member 330 and allows the inner shaft 360 to move through within the inner of the outer shaft 350.

Referring back to FIG. 2(*a*)-(*c*), FIG. 2(*b*) shows the embolic device 160 in a position to be released from the delivery catheter 110 according to an embodiment of the subject matter disclosed herein. When the delivery catheter 110 reaches the desired location (e.g. an aneurysm), the release of the maneuverable engagement member 140 may be actuated by a surgeon by pulling the linear member of the coupler. In this embodiment, the release of the maneuverable engagement member 140 occurs when the proximal end 132 of the coupler 130 is pulled toward the proximal end 112 of the delivery catheter 110. Then, the downward curve 154 of the maneuverable engagement member 140 may be pulled up from the lower locking window 152 and the tip 200 of the maneuverable engagement member 140 may be simultaneously pulled down from the locking window 150. The tip 200 of the maneuverable engagement member 140 may be further pulled down through the aperture 190 of the retaining mechanism 180 of the embolic device 160 and the downward curve 154 of the maneuverable engagement member 140 is completely taken out from the lower locking window 152. While the maneuverable engagement member 140 passes through the aperture 190, an edge 210 of the retaining mechanism 180 presses the upwardly curved or bent portion of the maneuverable engagement member 140 and a lower side of the cross bar 156 to make the curved or bent portion slightly straight such that the maneuverable engagement member 140 may be easily pulled out from the aperture 190. When the tip 200 of the maneuverable engagement member 140 passes through the lower of the cross bar 156, the cross bar 156 further pushes the upwardly curved or bent portion down, such that the tip 200 becomes straighter. This will help the maneuverable engagement member 140 to be pulled clearly inside of the delivery catheter 110 without dragging or scratching the inside wall of the catheter 110.

FIG. 2(*c*) shows the embolic device 160 being completely disengaged from the delivery catheter 110 in one embodiment. When the coupler 130 is pulled proximally and once the tip 200 of the maneuverable engagement member 140 is pulled out from the aperture 190 of the retaining mechanism 180, the embolic device 160 is disengaged from the distal end 120 of the delivery catheter 110. Then, the surgeon may carefully remove the entire delivery catheter 110 by pulling the delivery catheter 110 out from the artery to complete the procedure.

Figure 7:
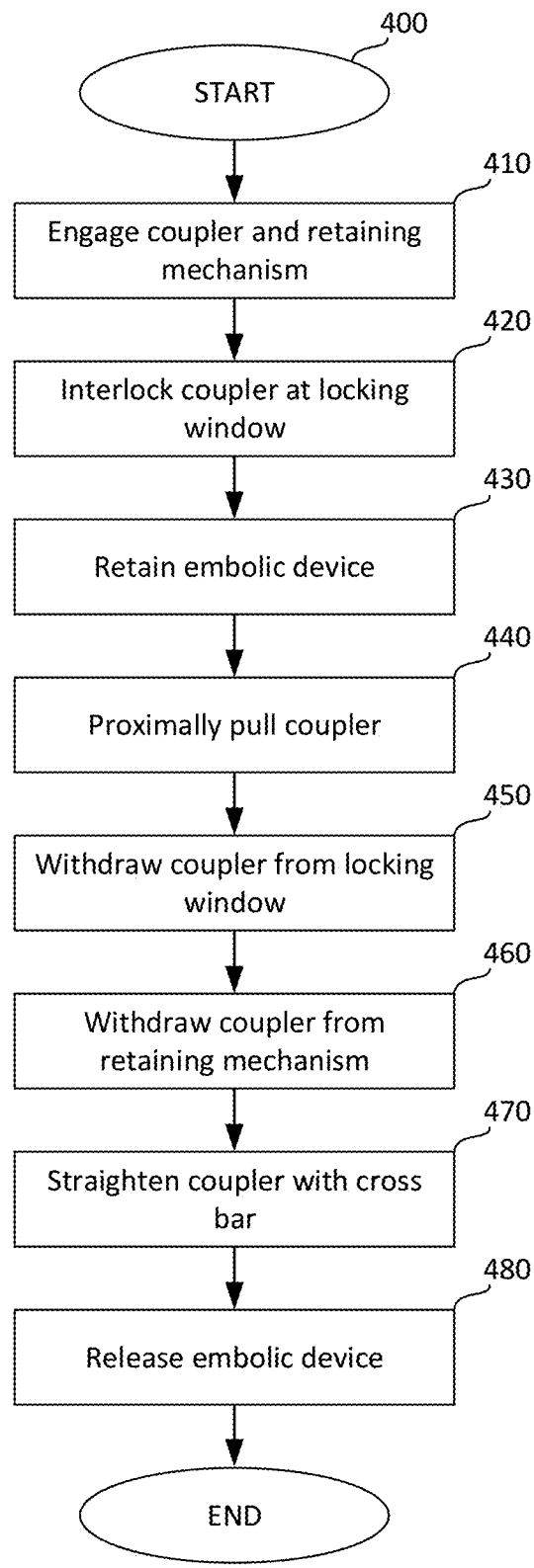
FIG. 7 is a flowchart for illustrating a method for delivering an embolic device according to an embodiment of the subject matter disclosed herein.

FIG. 7 is a flowchart for illustrating a method 400 for delivering an embolic device 160 according to an embodiment of the subject matter disclosed herein. Prior to insertion into any artery, the embolic device 160 may be engaged with the delivery catheter 110 by engaging the maneuverable engagement member 140 of the coupler 130 with the aperture 190 of the retaining mechanism 180 (step 410). The maneuverable engagement member 140 of the coupler 130 forms a curved shape and further extends into the upper locking window 150 and lower locking window 152 of the delivery catheter 110, such that the coupler 130 secures the embolic device 160 with the delivery catheter 110 (step 420). The delivery catheter 110 is inserted into an artery and navigated to the desired location of the artery with the embolic device 160 retained by the delivery catheter 110 (step 430). When the delivery catheter 110 reaches the desired location, the proximal end of the coupler 130 is pulled proximally (step 440). By pulling, the maneuverable engagement member 140 of the coupler 130 is withdrawn from the upper locking window 150 and lower locking window 152 (step 450). By further proximally pulling, the maneuverable engagement member 140 is further withdrawn from the aperture 190 of the retaining mechanism 180 (step 460). When the tip 200 of the maneuverable engagement member 140, especially the curved shape of the maneuverable engagement member 140 contacts a cross bar 156, the cross bar 156 pushes the maneuverable engagement member 140 down, such that the tip 200 is not dragged or scratched within the delivery catheter 110 (step 470). Once the tip 200 of the maneuverable engagement member 140 is completely withdrawn from the aperture 190, the embolic device 160 is released from the delivery catheter 110 and the delivery catheter is withdrawn from the artery (step 480).

Figure 8A:
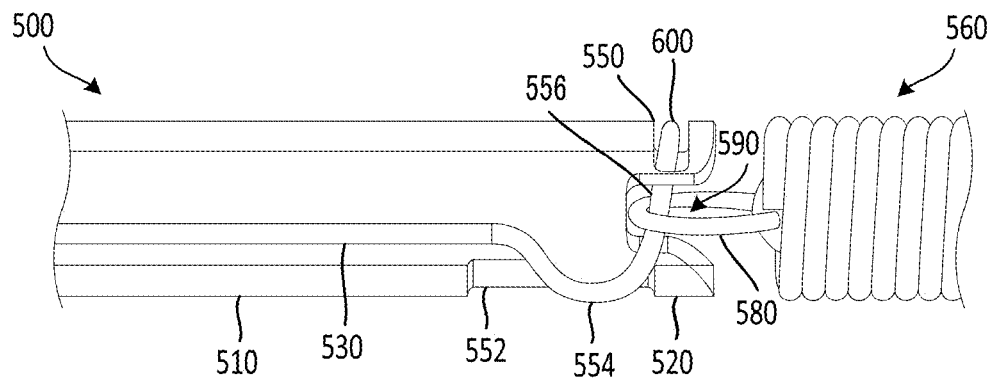
FIGS. 8(a)-(b) are diagrams of an embolic device delivery system according to a further embodiment of the subject matter disclosed herein.
Figure 8B:
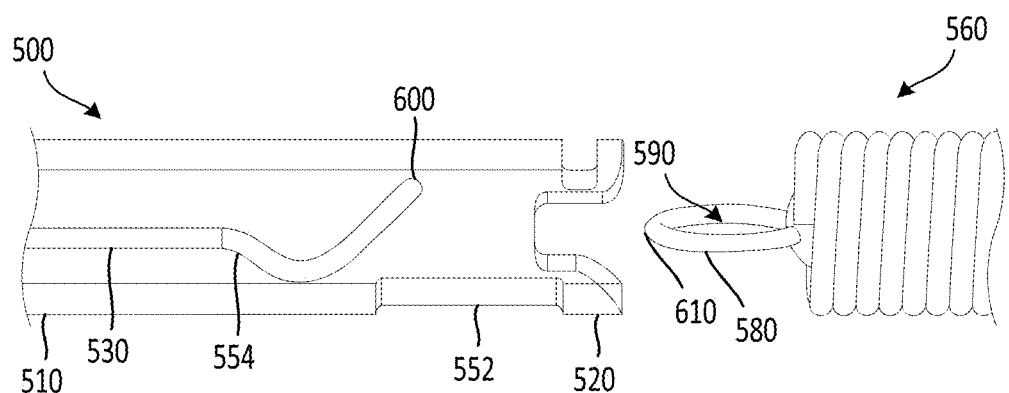

FIGS. 8(a)-(b) are diagrams of an embolic device delivery system 500 according to a further embodiment of the subject matter disclosed herein. An embolic device delivery system 500 may similarly include a delivery catheter 510, maneuverable coupler 530, and embolic device 560 with a retaining mechanism 580 formed integrally with the embolic device 560. The delivery catheter 510 may be a hollow tube to receive the maneuverable coupler 530 and the retaining ring 580 of the embolic device 560 within. Toward the distal end 520 of the delivery catheter 510, the maneuverable coupler 530 forms a U-shaped curve engagement member 540 to engage with the retaining mechanism 580. The engagement member 540 may be formed as a small diameter loop made of a shape-memory alloy, such as Nitinol, NiTi, or nickel titanium. The shape-memory alloy possesses super elasticity and unique memory characteristics of the original shape. Thus, the shape-memory alloy may be stretched and maintained in the stretched phase; however, once the alloy is released from the stretch, the alloy will return back to the original shape. The maneuverable engagement member 540 may be further configured to be become more/less rigid and/or more/less flaccid when exposed to heat, electricity, or physical force. As discussed with respect to FIG. 8(b), this allows the maneuverable coupler 530 to engage, maneuver and disengage an embolic device 560 during an embolic device delivery procedure.

The delivery catheter 510 forms an upper locking window 550 on one side of the interior wall of the hollow tube near the distal end 520 of the delivery catheter 510 and a lower locking window 552 on the other side of the interior wall of the hollow tube near the distal end 520 of the delivery catheter 510. In this embodiment, the upper locking window 552 is located relatively closer to the distal end 520 of the delivery catheter 510 compared to the upper locking window 150 of the embolic device delivery system 100 described in FIGS. 2(a)-(c). In one embodiment, the maneuverable engagement member 540 may form a U-shaped curve 554 and the downward curve 554 of the maneuverable engagement member 540 may be maintained with the locking features by the upper locking window 550 and the lower locking window 552. In this configuration, the bottom of the downward curve 554 of the maneuverable engagement member 540 may be maintained within the lower locking window 552 and a tip 600 of the maneuverable engagement member 540 may be maintained within the upper locking window 550 while navigating the delivery catheter 510 into an artery. In this locking position, an elongated portion 556 of the maneuverable engagement member 540 between the U-shaped curve 554 and the tip 600 forms almost a straight line and the tip 600 may stably extend into the upper locking window 550 in a vertical position. In another embodiment, the upper locking window 550 is located nearer to the distal end 520 of the delivery catheter 510 than the lower locking window 552 is to the distal end 520 of the delivery catheter 510 such that the maneuverable engagement member 540 is locked with the upper locking window 150 and the lower locking window 552 at the distal end 520 of the delivery catheter 510. The maneuverable engagement member 540 extends through the upper locking window 550 and the lower locking window 552 of the delivery catheter 510 similar to the upper locking window 150 in the left elevational view described in FIG. 3 and the lower locking window 152 in the front elevational view described in FIG. 4.

When the embolic device 560 is in a position coupled to the delivery catheter 510 (see FIG. 8(a)), the maneuverable engagement member 540 engages with the aperture 590 of the retaining mechanism 580 and may be further extended through the upper locking window 550 located above the position of the aperture 590 of the retaining mechanism 580 and the lower locking window 552 to secure the maneuverable engagement member 540 in the position. Once the maneuverable engagement member 540 is shaped in the upwardly curved position, the maneuverable engagement member 540 maintains its shape until any physical force is applied to the maneuverable engagement member 540. The upwardly curved shape of the maneuverable engagement member 540 may be formed by physically bending the maneuverable engagement member 540, such as by hand, or by maneuvering the distal end 520 of the maneuverable engagement member 540 to extend the maneuverable engagement member 540 through the aperture 590 such that the straight original configuration is deformed into the curved shape. In various embodiments, the upper locking window 550 and lower locking window 552 may be formed as a rectangular shape, elliptical shape, oval shape, or round shape. In a still further embodiment, the width of the locking window 550 may be slightly wider than the width of the tip 600 of the maneuverable engagement member 540. As such, the inside of the locking window 550 allows limited movement of the tip 600 to move around such that the tip 600 is secured in the locking window 550.

FIG. 8(b) shows the embolic device 560 in a position to be released from the delivery catheter 510 according to an embodiment of the subject matter disclosed herein. When the delivery catheter 510 reaches the desired location (e.g. an aneurysm), the release of the maneuverable engagement member 540 from the retaining mechanism 580 may be actuated by a surgeon by pulling the linear member of the maneuverable engagement member 540. In this embodiment, the release of the maneuverable engagement member 540 occurs when the proximal end (not shown) of the maneuverable engagement member 540 is pulled toward the proximal end of the delivery catheter 510. Then, the downward curve 554 of the maneuverable engagement member 540 may be pulled up from the lower locking window 552 and the tip 600 of the maneuverable engagement member 540 may be simultaneously pulled down from the locking window 550. The tip 600 of the maneuverable engagement member 540 may be further pulled down through the aperture 590 of the retaining mechanism 580 of the embolic device 560 and the downward curve 554 of the maneuverable engagement member 540 is completely taken out from the lower locking window 552. While the maneuverable engagement member 540 passes through the aperture 590, an edge 610 of the retaining mechanism 580 presses the upwardly curved or bent portion of the maneuverable engagement member 540 to make the curved or bent portion slightly straight such that the maneuverable engagement member 540 may be easily pulled out from the aperture 590. When the maneuverable engagement member 540 is pulled proximally and once the tip 600 of the maneuverable engagement member 540 is pulled out from the aperture 590 of the retaining mechanism 580, the embolic device 560 is disengaged from the delivery catheter 510. Then, the surgeon may carefully remove the entire delivery catheter 510 by pulling the delivery catheter 510 out from the artery to complete the procedure.

Figure 9A:
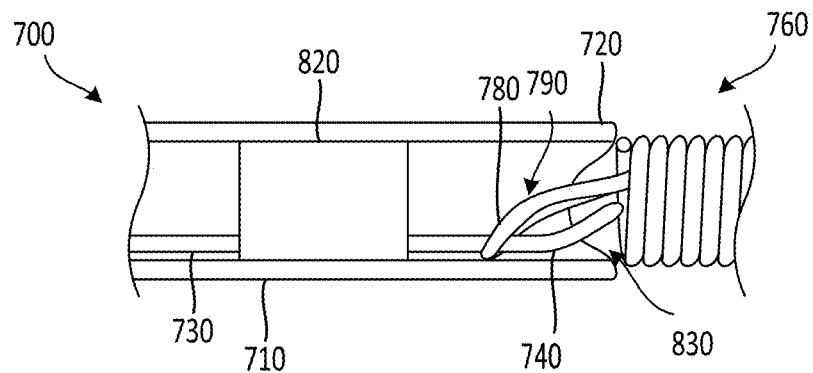
FIGS. 9(a)-(c) are diagrams of an embolic device delivery system according to a still further embodiment of the subject matter disclosed herein.
Figure 9B:
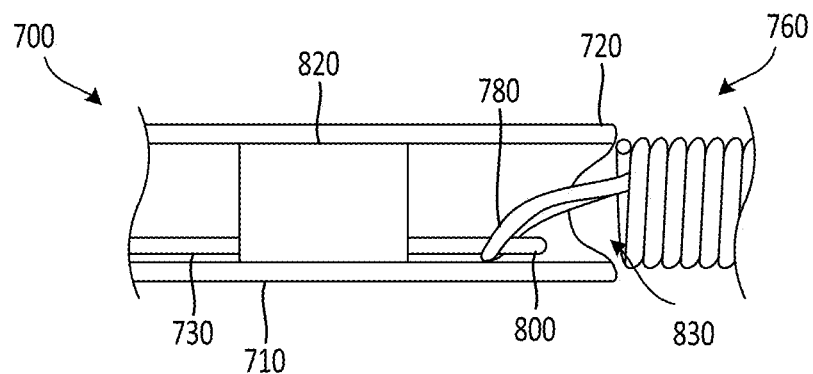
Figure 9C:
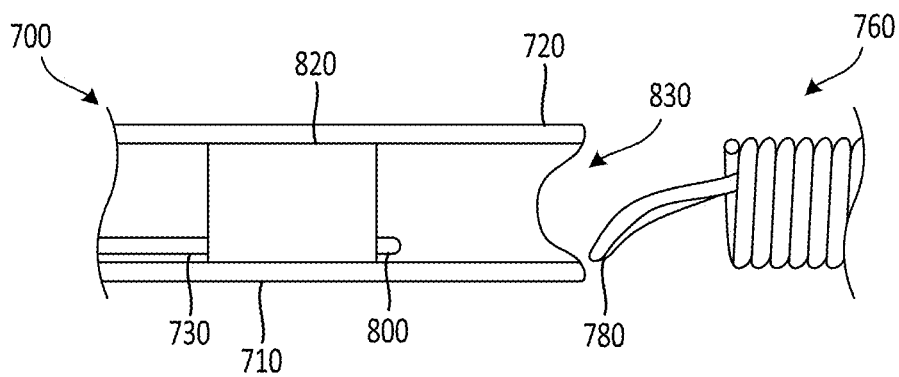
Figure 10A:
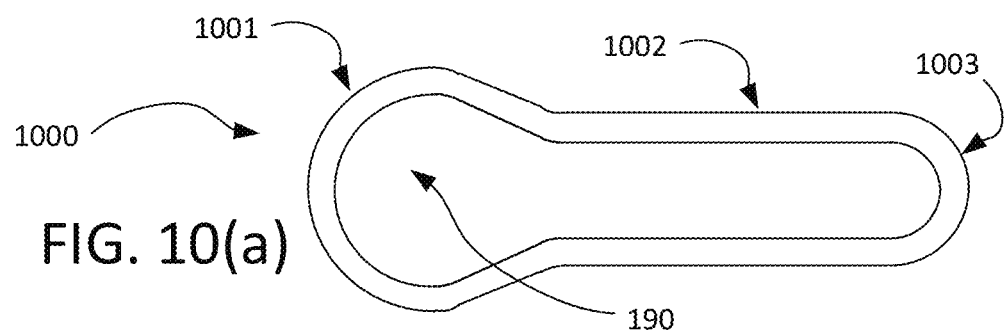
FIGS. 10(a)-(c) are diagrams of an embolic device suited for ease of delivery and placement according to an embodiment of the subject matter disclosed herein.
Figure 10B:
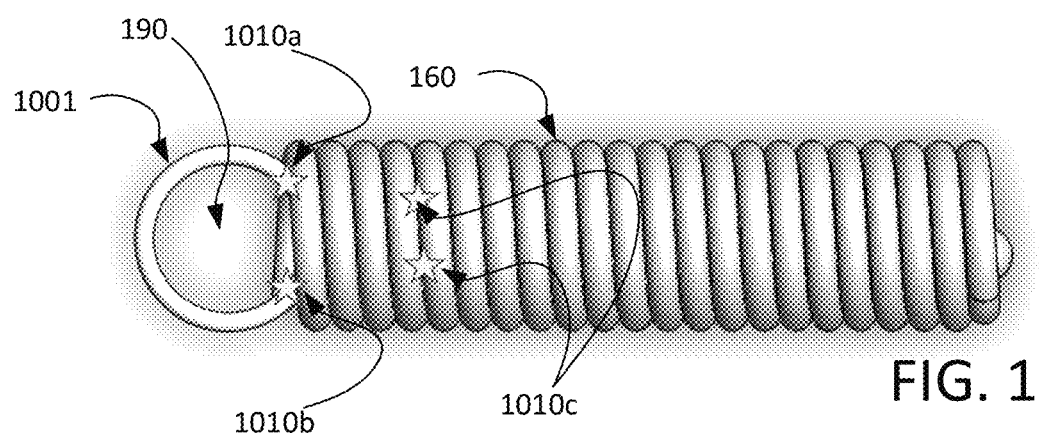
Figure 10C:
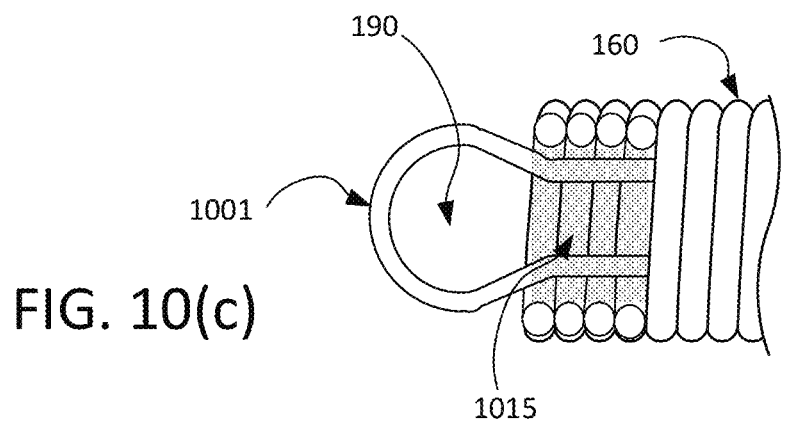

FIGS. 9(a)-(c) are diagrams of an embolic device delivery system 700 according to a still further embodiment of the subject matter disclosed herein. An embolic device delivery system 700 may similarly include a delivery catheter 710, maneuverable coupler 730, and embolic device 760 with a retaining mechanism 780 formed integrally with the embolic device 760. The delivery catheter 710 may be a hollow tube to receive the maneuverable coupler 730 and the retaining ring 780 of the embolic device 760 within. Toward the distal end 720 of the delivery catheter 710, the maneuverable coupler 730 forms a U-shaped curve open loop engagement member 740 to engage with the retaining mechanism 780. In one embodiment, the maneuverable engagement loop 740 may form an upward U-shaped curve and the retaining mechanism 780 may form a downward curve such that the maneuverable engagement loop 740 can engage with the retaining 780 mechanism in an interlocking position. The engagement loop 740 may be formed as a small diameter loop made of a shape-memory alloy, such as Nitinol, NiTi, or nickel titanium. The shape-memory alloy possesses super elasticity and unique memory characteristics of the original shape. Thus, the shape-memory alloy may be stretched and maintained in the stretched phase; however, once the alloy is released from the stretch, the alloy will return back to the original shape. The maneuverable engagement loop 740 may be further configured to become more/less rigid and/or more/less flaccid when exposed to heat, electricity, or physical force. As discussed with respect to FIGS. 9(*b*) and 9(*c*), this allows the maneuverable coupler 730 to engage, maneuver and disengage an embolic device 760 during an embolic device delivery procedure. Within the hollow tube of the delivery catheter 710, a loop reducer 820 may be placed for the maneuverable engagement loop 740 to maintain the location inside of the delivery catheter 710. The loop reducer 820 has an opening (not shown) to receive the linear member of the maneuverable coupler 730 extending from the proximal end (not shown) to the distal end 720 of the delivery catheter 710. In a further embodiment, the distal end 720 of the delivery catheter may have a cutout 830 for the retaining mechanism 580 of the embolic device can be maintained without any difficulties.

When the embolic device 760 is in a position coupled to the delivery catheter 710 (see FIG. 9(*a*)), the maneuverable engagement loop 740 may be simply extended through the aperture 790 of the retaining mechanism 780. Once the maneuverable engagement loop 740 is shaped in the upwardly curved position, the maneuverable engagement loop 740 maintains its shape until any physical force is applied to the maneuverable engagement loop 740. In one embodiment, the upwardly curved shape of the maneuverable engagement loop 740 may be formed by physically bending the maneuverable engagement loop 740, such as by hand, or by maneuvering the distal end 720 of the maneuverable engagement loop 740 to extend the maneuverable engagement loop 740 through the aperture 790 such that the straight original configuration is deformed into the curved shape. In a further embodiment, the width of the maneuverable engagement loop 740 may be slightly narrower than the width of the aperture 790 of the retaining mechanism 780. As such, the inside of the aperture 790 of the retaining mechanism 780 allows limited movement of the maneuverable engagement loop 740 to move around such that the maneuverable engagement loop 740 is secured in the retaining mechanism 780.

FIG. 9(*b*) shows the embolic device 760 in a position to be released from the delivery catheter 710 according to a still further embodiment of the subject matter disclosed herein. When the delivery catheter 710 reaches the desired location (e.g. an aneurysm), the release of the maneuverable engagement loop 740 from the retaining mechanism 780 may be actuated by a surgeon by pulling the linear member of the maneuverable coupler 730. In this embodiment, the release of the maneuverable engagement loop 740 occurs when the linear member of the maneuverable coupler 730 is pulled toward the proximal end (not shown) of the delivery catheter 710. Then, the maneuverable engagement loop 740 may be pulled from the aperture 790 of the retaining mechanism 780 of the embolic device 760 and go through the opening of the loop reducer 820. While the maneuverable engagement loop 740 passes through the opening of the loop reducer 820, an edge 800 of the maneuverable engagement loop 740 presses the open loop of the maneuverable engagement loop 740 to make the loop portion closed such that the maneuverable engagement loop 740 may be easily pulled out from the opening of the loop reducer 820.

FIG. 9(*c*) shows the embolic device 760 being completely disengaged from the delivery catheter 710 in one embodiment. When the maneuverable engagement loop 740 is pulled proximally and once the tip 800 of the maneuverable engagement loop 740 is pulled out from the aperture 790 of the retaining mechanism 780, the embolic device 760 is disengaged from the delivery catheter 710. Then, the surgeon may carefully remove the entire delivery catheter 710 by pulling the delivery catheter 710 out from the artery to complete the procedure.

Embolic Device Suited for Ease of Use in Delivery System

FIGS. 10(*a*)-(*c*) are diagrams of an embolic device suited for ease of delivery and placement according to an embodiment of the subject matter disclosed herein. The various embodiments described with respect to FIGS. 10(*a*)-(*c*) are each examples of embolic devices that are suited to be used with the embolic device delivery system 100 as described above with respect to FIGS. 1-9. Some of these embodiments may be better suited for different operations and different performance characteristics. The various embodiments are detailed below in relation to each of FIGS. 10(*a*)-(*c*). As such, each embolic device described herein includes a retaining mechanism 180 having an aperture 190 (as enumerated in FIGS. 2*a/b*).

FIG. 10(*a*) shows a diagram of a retaining mechanism 1000 (e.g., a wire form) suited to be used as a portion of an embolic device and coupled to a proximal end of an embolic device. The retaining mechanism 1000 takes the shape of a closed metal loop that may be inserted and secured in one or more ways to a proximal end of an embolic device. Further, the retaining mechanism 1000 serves the purpose in the overall embolic device as is described above with respect to the retaining mechanism 180 as discussed above with respect to FIGS. 1-9. In the retaining mechanism 1000 of FIG. 10(*a*), the aperture 190 is formed at a major end 1001 of the retaining mechanism 1000. The retaining mechanism 1000 in FIG. 10(*a*) includes two ends including the aforementioned major end 1001 and a minor end 1003. The major/minor end distinction only applies to relative size of each end as one can see a difference in relative diameter between the major end 1001 and the minor end 1003. The major end 1001 and minor end 1003 are coupled together via an elongated middle section 1002 that is relatively linear in coupling the semicircular shapes of the major end 1001 and the minor end 1003.

The retaining mechanism 1001 as shown in FIG. 10(*a*) is suited to be securely affixed to a proximal end of an embolic device (not shown in FIG. 10(*a*)) such that the aperture 190 formed at the major end 1001 of the retaining mechanism 1000 is suited to be engaged by a coupler (e.g., coupler 130 as shown in FIG. 2(*a*)) as described above. Thus, the coupler (not shown in FIG. 10(*a*)) may engage the retaining mechanism 1000 and push/pull (or otherwise maneuver) the attached embolic device using the maneuverability aspects of the embolic device delivery system as discussed previously. The manner in which the retaining mechanism 1000 is coupled to the embolic device varies as is discussed in the various embodiments described next with respect to FIGS. 10(*b*)-(*c*).

FIG. 10(*b*) shows a diagram of a first manner of coupling the retaining mechanism 1000 as shown in FIG. 10(*a*) to an embolic device 160 according to one embodiment of the subject matter discussed herein. In this embodiment, the retaining mechanism 1000 may have its minor end 1003 inserted into the end of a primary wind of an embolic device 160. The primary wind of the embolic device 160 has a pitch such that the turns/pitches most proximal to the end that engages the wire form 1000 are slightly opened (as one can see as the retaining mechanism 1000 positioned through the last 3-5 pitch turns becomes slightly larger in diameter). Once positioned, a laser (not shown) may be fired directly between the slightly opened pitch, which causes the retaining mechanism 1000 and interior of the primary winding of the most proximal end of the embolic device to fuse together. The fusing is indicated by the stars 1010*a* and 1010*b*. In some embodiments, the retaining mechanism 1000 may also be fused slightly away from the central axis of the primary winding of the embolic device so there is enough of a line of site through the primary winding for also realizing one or more fuse points in the interior of the embolic device. This interior fuse point is indicated by the two fuse points 1010*c*.

FIG. 10(*c*) shows a diagram of a second manner of coupling the retaining mechanism 1000 as shown in FIG. 10(*a*) to an embolic device 160 according to one embodiment of the subject matter discussed herein. In this embodiment, the retaining mechanism 1000 is affixed to the primary winding of the embolic device using adhesive 1015. In this manner, an adhesive may be placed inside the primary winding at the proximal end of the embolic device 160 such that the minor end 1003 of the retaining mechanism 1000 may be inserted into the primary winding where the adhesive is placed. Then, the adhesive 1015 may cure (e.g., dry, or otherwise harden, for example, through application of ultra-violet (UV) light) and subsequently secure the retaining mechanism 1000 to the primary winding of the embolic device 160.

Figure 11:
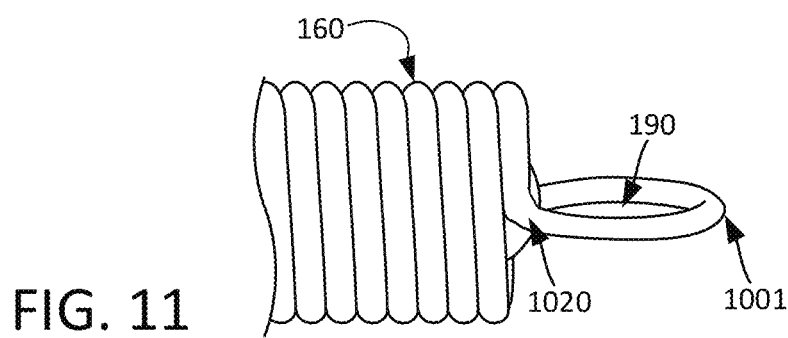
FIG. 11 is a diagram of a monolithic embolic device suited for ease of delivery and placement according to an embodiment of the subject matter disclosed herein.

FIG. 11 shows a diagram of a monolithic solution wherein a major end 1001 of the retaining mechanism 1000 is part and parcel (e.g., integral) with the primary winding of the embolic device 160. As shown, the primary winding may include an end (e.g., the proximal end) that includes a bent-out portion 1020 that forms the major end 1001 of a retaining mechanism in forming an aperture 190 that may engage a coupler of an embolic device delivery system as discussed above. This solution provides a monolithic solution (e.g., the primary winding also includes the bent-out portion 1020 that forms a major end 1001 of a retaining mechanism 1000) and therefore, fusing, welds, and/or adhesives are not needed.

FIGS. 12(*a*)-(*d*) are diagrams of additional embolic devices suited for ease of delivery and placement according to still further embodiments of the subject matter disclosed herein. In these embodiments, a retaining mechanism may be used in conjunction with a slotted metal tube for assisting in holding the retaining mechanism in place. In this manner, the slotted metal tube provides a more robust portion of the overall embolic device so that the retaining mechanism may be flash welded (e.g., fused) to a portion of the embolic device that will not be compromised by the heat generated during the fusing procedure. These and other aspects are discussed below with respect to FIGS. 12(*a*)-(*d*).

FIG. 12(*a*) shows a diagram of a first embodiment of a retaining mechanism 1200 suited for use with a slotted metal tube portion of an embolic device (not shown in FIG. 12(*a*)). The retaining mechanism 1200 includes a major end 1204 that feature an aperture 190 form by a closed end loop structure. However, different form the retaining mechanism 1000 as shown in FIG. 10(*a*), there is no minor end. Instead, the retaining mechanism 1200 includes a base portion 1212 that includes a number of features for assisting is securing the retaining mechanism to the slotted metal tube as well as to a coupler wire and/or the primary winding.

A first feature of the base portion 1212 of the retaining mechanism 1200 includes first and second protrusions 1205*a/b* that are positioned adjacent to the major end 1204 and offset enough to protrude through slots of a metal slotted tube. In this manner, the protrusions 1205*a/b* provide purchase to the slotted metal tube in assisting with securing the retaining mechanism into place. Further, a second feature includes a coupler orifice 1210 suited for receiving a proximal end of a coupler wire 1214 through the coupler orifice 1210. In this manner, the coupler wire 1214 may be threaded through the coupler orifice 1210 toward the aperture 190. Then, the coupler wire 1214 may be formed into a suture 1215 to prevent the coupler wire 1214 from being maneuvered back out of the coupler orifice 1210 of the base portion 1212. This suture 1215 then secures the coupler wire 1214 to the overall retaining mechanism 1200. Likewise, if the retaining mechanism 1200 is then secured to a slotted metal tube (e.g., because the protrusions 1205*a/b* are positioned in slots of a slotted metal tube), the overall embolic device may be maneuvered using an embolic device delivery system having a capability of manipulating the coupler wire 1214.

FIG. 12(*b*) shows a diagram of a second embodiment of a retaining mechanism 1250 suited for use with a slotted metal tube portion of an embolic device (not shown in FIG. 12(*b*)). The retaining mechanism 1250 includes a major end 1204 that feature an aperture 190 form by a closed end loop structure. Similar to that which was discussed above, this retaining mechanism 1250 is different form the retaining mechanism 1000 as shown in FIG. 10(*a*), as there is no minor end. Instead, the retaining mechanism 1250 includes a base portion 1212 that includes a number of features for assisting is securing the retaining mechanism to the slotted metal tube as well as to a coupler wire and/or the primary winding.

A first feature of the base portion 1212 of the retaining mechanism 1250 again includes first and second protrusions 1205*a/b* that are positioned adjacent to the major end 1204 and offset enough to protrude through slots of a metal slotted tube. In this manner, the protrusions 1205*a/b* provide purchase to the slotted metal tube in assisting with securing the retaining mechanism into place. Further, a second feature includes a slotted coupler orifice 1255 having first and second internal protrusions 1253*a/b* suited for receiving a proximal end of a coupler wire 1214 through the slotted coupler orifice 1255. In this manner, the coupler wire 1214 may be threaded through the slotted coupler orifice 1255 toward the aperture 190. Then, the coupler wire 1214 may be formed into a suture 1215 to prevent the coupler wire 1214 from being maneuvered back out of the slotted coupler orifice 1255 of the base portion 1212. This suture 1215 then secures the coupler wire 1214 to the overall retaining mechanism 1250. Likewise, if the retaining mechanism 1250 is then secured to a slotted metal tube (e.g., because the protrusions 1205*a/b* are positioned in slots of a slotted metal tube), the overall embolic device may be maneuvered using an embolic device delivery system having a capability of manipulating the coupler wire 1214. The retaining mechanisms 1200 and 1250 of FIGS. 12(*a*) and 12(*b*) may be utilized with an embolic device 160 having a slotted metal tube as discussed next with respect to FIGS. 12(*c*) and 12(*d*).

FIG. 12(*c*) shows a diagram of the retaining mechanism 1200 of FIG. 12(*a*) coupled with a slotted metal tube as discussed above according to an embodiment of the subject matter disclosed herein. As skilled artisan understands that the retaining mechanism 1250 of FIG. 12(*b*) as described above may be also be interchangeably with the retaining mechanism 1200 as shown in FIGS. 12(*c*) and 12(*d*). However, the retaining mechanism 1200 will only be referenced strictly for ease of illustration in in FIGS. 12(*c*) and 12(*d*). Thus, one can see that the slotted metal tube 1270 includes a first visible slot 1271 having one protrusion 1205*a* of the retaining mechanism 1200 inserted therein. Though it cannot be seen in this view, it is understood that the second protrusion 1205*b* protrudes though a second slot on the opposite side of the slotted metal tube 1270 in a similar manner. As the slotted metal tube 1271 is more robust than the primary winding of any attached embolic device, a fusing laser may be aimed at the protrusion 1205*a* protruding through the first slot 1271 such that the protrusion 1205*a* and the slot 1271 are fused together. A similar fusing may occur with respect to the unseen slot and protrusion 1205*b*. Therefore, the retaining mechanism 1200 and the slotted metal tube 1270 may be maneuvered as one cohesive unit. As discussed next, if the slotted metal tube 1270 is coupled to an embolic device (not shown in FIG. 12(*c*)), the entire assembly may be maneuvered by engaging the retaining mechanism 1200.

FIG. 12(*d*) shows a diagram of the slotted metal tube 1270 of FIG. 12(*c*) attached to an embolic device 160 according to an embodiment of the subject matter disclosed herein. As alluded to previously, the combination of the slotted metal tube 1270 and the retaining mechanism 1200 may be affixed to a proximal end of an embolic device. In one embodiment, this may be accomplished using a laser to create a flash weld 1290 between one end of the slotted metal tube 1270 and an end of the primary winding of the embolic device 160. In this manner, the assembly may be maneuvered as discussed in several embodiment above.

Figure 13:
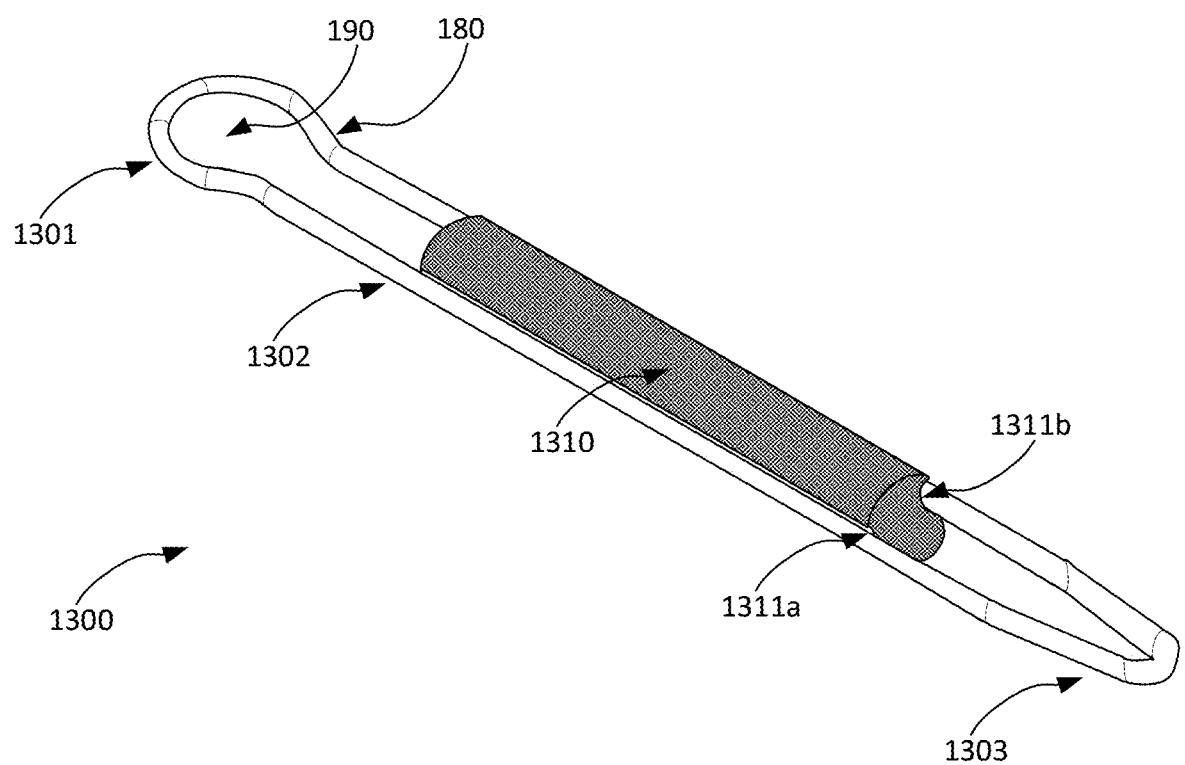
FIG. 13 is a diagram of another embodiment of an embolic device suited for ease of delivery and placement according to an embodiment of the subject matter disclosed herein.

FIG. 13 is a diagram of another embodiment of a retaining mechanism 1300 an embolic device suited for ease of delivery and placement according to an embodiment of the subject matter disclosed herein. This embodiment as described with respect to FIG. 13 is another example of a retaining mechanism 1300 that is suited to be used with the embolic device delivery system 100 as described above with respect to FIGS. 1-9. As before, this embolic device (not shown) described here includes a retaining mechanism 1300 having an aperture 190 (as enumerated in FIGS. 2*a/b*).

FIG. 13 shows a diagram of a retaining mechanism 1300 (e.g., a wire form) suited to be used as a portion of an embolic device (not shown) whereby this retaining mechanism is coupled to a proximal end of an embolic device (as shown with respect to the embodiment of FIGS. 10(*a*)-(*c*). The retaining mechanism 1300 takes the shape of a closed metal loop that may be inserted and secured in one or more ways to a proximal end of an embolic device. Further, the retaining mechanism 1300 serves the purpose in the overall embolic device as is described above with respect to the retaining mechanism 180 as discussed above with respect to FIGS. 1-9. In the retaining mechanism 1300 of FIG. 13, the aperture 190 is formed at a major end 1301 of the retaining mechanism 1300. The retaining mechanism 1300 in FIG. 13 includes two ends including the aforementioned major end 1301 and a minor end 1303. The major/minor end distinction only applies to relative size of each end as one can see a difference in relative diameter between the major end 1301 and the minor end 1303. The major end 1301 and minor end 1303 are coupled together via an elongated middle section 1302 that is relatively linear in coupling the semicircular shapes of the major end 1301 and the minor end 1303. Further, in this embodiment, the minor end 1303 may include a tapering or narrowing shape culminating in the minor end 1303.

The retaining mechanism 1301 as shown in FIG. 13 further comprises a central support structure 1310 designed to provide additional physical support for the overall loop structure of the retaining mechanism 1300. The support structure resembles an elongated tube having a first curved pocket 1311*a* suited to secure a first side of the elongated middle section 1302 and a second curved pocket 1311*b* suited to secure a second side of the elongated middle section 1302. The central support structure 1310 provides additional support for the overall retaining mechanism 1300 to be securely affixed to a proximal end of an embolic device (not shown in FIG. 13) such that the aperture 190 formed at the major end 1301 of the retaining mechanism 1300 is suited to be engaged by a coupler (e.g., coupler 130 as shown in FIG. 2(*a*)) as described above. Thus, the coupler (not shown in FIG. 13) may engage the retaining mechanism 1300 and push/pull (or otherwise maneuver) the attached embolic device using the maneuverability aspects of the embolic device delivery system as discussed previously. The manner in which the retaining mechanism 1300 is coupled to the embolic device varies as is discussed above in the various embodiments described with respect to FIGS. 10(*b*)-(*c*).

All references, including publications, patent applications, and patents, cited herein are hereby incorporated by reference to the same extent as if each reference were individually and specifically indicated to be incorporated by reference and/or were set forth in its entirety herein.

The use of the terms "a" and "an" and "the" and similar referents in the specification and in the following claims are to be construed to cover both the singular and the plural, unless otherwise indicated herein or clearly contradicted by context. The terms "having," "including," "containing" and similar referents in the specification and in the following claims are to be construed as open-ended terms (e.g., meaning "including, but not limited to,") unless otherwise noted. Recitation of ranges of values herein are merely intended to serve as a shorthand method of referring individually to each separate value inclusively falling within the range, unless otherwise indicated herein, and each separate value is incorporated into the specification as if it were individually recited herein. All methods described herein can be performed in any suitable order unless otherwise indicated herein or clearly contradicted by context. The use of any and all examples, or exemplary language (e.g., "such as") provided herein, is intended merely to better illuminate embodiments and does not pose a limitation to the scope of the disclosure unless otherwise claimed. No language in the specification should be construed as indicating any non-claimed element as essential to each embodiment of the present disclosure.

Different arrangements of the components depicted in the drawings or described above, as well as components and steps not shown or described are possible. Similarly, some features and sub-combinations are useful and may be employed without reference to other features and sub-combinations. Embodiments have been described for illustrative and not restrictive purposes, and alternative embodiments will become apparent to readers of this patent. Accordingly, the present subject matter is not limited to the embodiments described above or depicted in the drawings, and various embodiments and modifications can be made without departing from the scope of the claims below.

What is claimed is:

1. An embolic device, comprising:
    a primary winding having a coiled member forming a hollow tube structure having a proximal end and a distal end;
    a slotted metal tube affixed to the primary winding at one of the ends and having a plurality of slots positioned in a body of the slotted metal tube; and
    a retaining mechanism having a plurality of protrusions and an aperture, the retaining mechanism affixed to the slotted metal tube wherein each slot in the body of the slotted metal tube is coupled to a respective protrusion of the retaining mechanism by a flash weld, the retaining mechanism securely affixed to the slotted metal tube such that the aperture is exposed adjacent to the slotted metal tube.

2. The embolic device of claim 1, wherein the plurality of slots comprises two slots.

3. The embolic device of claim 1, further comprising a coupler orifice disposed in a base portion of the retaining mechanism suited for receiving a coupler wire from an embolic procedure system.

4. The embolic device of claim 3, wherein the coupler orifice comprises a slotted coupler orifice having the protrusions comprised of first and second protruding members disposed adjacent to a slot of the slotted coupler orifice.

5. The embolic device of claim 1, further comprising a flash weld disposed between the primary winding and the slotted metal tube.

6. The embolic device of claim 1, further comprising adhesive disposed between the primary winding and the slotted metal tube.

7. An embolic device, comprising:
    a primary winding having a coiled member forming a hollow tube structure having a proximal end and a distal end; and
    a retaining mechanism having a major end forming an aperture and a minor end, the retaining mechanism having a plurality of protrusions affixed to the hollow tube structure by slots in the body of the hollow tube structure, wherein each slot in the body of the hollow tube structure is coupled to a respective protrusion of the retaining mechanism with a respective flash weld and wherein the minor end is disposed inside the hollow tube and the major end is disposed outside of the hollow tube.

8. The embolic device of claim 7, further comprising adhesive configured to secure the minor end of the retaining mechanism to the inside of the hollow tube.

9. The embolic device of claim 7, further comprising at least one flash weld between a portion of the minor end of the retaining mechanism and the inside of the hollow tube of the primary winding.

10. The embolic device of claim 7, further comprising at least one flash weld between a portion of the major end of the retaining mechanism and an end of the primary winding.

11. An embolic procedure system, comprising:
    an embolic device, including:
        a primary winding having a coiled member forming a hollow tube structure having a proximal end and a distal end;
        a slotted metal tube affixed to the primary winding at one of the ends and having a plurality of slots positioned in a body of the slotted metal tube; and
        a retaining mechanism having a plurality of protrusions and an aperture, the retaining mechanism affixed to the slotted metal tube wherein each slot in the body of the slotted metal tube is coupled to a respective protrusion of the retaining mechanism via a flash weld, the retaining mechanism securely affixed to the slotted metal tube such that the aperture is exposed adjacent to the slotted metal tube;
    a catheter having an elastic coupler disposed therein and configured to engage the aperture of the embolic device; and
    an actuator operably coupled to the coupler and configured to maneuver the coupler to engage the embolic device.

12. The embolic procedure system of claim 11, further comprising a flash weld disposed between the primary winding and the slotted metal tube.

13. The embolic procedure system of claim 11, further comprising adhesive disposed between the primary winding and the slotted metal tube.

14. An embolic procedure system, comprising:
    an embolic device, including:
        a primary winding having a coiled member forming a hollow tube structure having a proximal end and a distal end; and
        a retaining mechanism having a major end forming an aperture and a minor end, the retaining mechanism having a plurality of protrusions, the retaining mechanism affixed to the hollow tube structure by slots in the body of the hollow tube structure, wherein each slot in the body of the hollow tube structure is coupled to a respective protrusion of the retaining mechanism with a respective flash weld and wherein the minor end is disposed inside the hollow tube and the major end is disposed outside of the hollow tube;
    a catheter having an elastic coupler disposed therein and configured to engage the aperture of the embolic device; and
    an actuator operably coupled to the coupler and configured to maneuver the coupler to engage the embolic device.

15. The embolic procedure system of claim 14, further comprising adhesive configured to secure the minor end of the retaining mechanism to the inside of the hollow tube.

16. The embolic procedure system of claim 14, further comprising at least one flash weld between a portion of the minor end of the retaining mechanism and the inside of the hollow tube of the primary winding.

17. The embolic procedure system of claim 14, further comprising at least one flash weld between a portion of the major end of the retaining mechanism and an end of the primary winding.

* * * * *